(12) United States Patent
Khanmamedova et al.

(10) Patent No.: US 8,772,192 B2
(45) Date of Patent: Jul. 8, 2014

(54) GERMANIUM SILICALITE CATALYST AND METHOD OF PREPARATION AND USE

(75) Inventors: Alla Khanmamedova, Sugar Land, TX (US); Scott Stevenson, Houston, TX (US); Dustin Farmer, Houston, TX (US); Mike Mier, Waller, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 13/537,184

(22) Filed: Jun. 29, 2012

(65) Prior Publication Data

US 2014/0005453 A1 Jan. 2, 2014

(51) Int. Cl.
*B01J 29/06* (2006.01)

(52) U.S. Cl.
USPC ............... 502/60; 502/77; 502/232; 502/234; 502/236; 502/242; 423/713

(58) Field of Classification Search
USPC .................... 502/60, 77, 232, 234, 236, 242; 423/713
See application file for complete search history.

(56) References Cited

U.S. PATENT DOCUMENTS

| | | | |
|---|---|---|---|
| 3,640,681 A * | 2/1972 | Pickert .......................... | 423/713 |
| 4,061,724 A | 12/1977 | Grose et al. | |
| 4,410,501 A | 10/1983 | Taramasso et al. | |
| 4,645,586 A | 2/1987 | Buss | |
| 4,897,177 A | 1/1990 | Nadler | |
| 4,962,250 A | 10/1990 | Dessau et al. | |
| 5,155,074 A | 10/1992 | Mohr | |
| 5,227,557 A | 7/1993 | Bournonville et al. | |
| 5,268,522 A | 12/1993 | Bournonville et al. | |
| 5,371,307 A | 12/1994 | Guth et al. | |
| 5,456,822 A | 10/1995 | Marcilly et al. | |
| 5,672,796 A | 9/1997 | Froment et al. | |
| 5,869,706 A | 2/1999 | Dartt et al. | |
| 5,885,439 A | 3/1999 | Glover | |
| 5,958,216 A | 9/1999 | Glover | |
| 5,977,009 A | 11/1999 | Faraj | |
| 6,040,259 A | 3/2000 | Mohr et al. | |
| 6,358,400 B1 | 3/2002 | Bogdan et al. | |
| 6,784,333 B2 | 8/2004 | Juttu et al. | |
| 7,029,650 B1 * | 4/2006 | Juttu et al. .................... | 423/705 |
| 7,186,871 B2 | 3/2007 | Mitchell et al. | |
| 7,247,593 B2 | 7/2007 | Juttu et al. | |
| 7,439,204 B2 * | 10/2008 | McMinn et al. ................ | 502/74 |
| 7,449,168 B2 | 11/2008 | Juttu et al. | |
| 7,745,675 B2 * | 6/2010 | Ellis et al. ..................... | 585/418 |
| 7,902,413 B2 | 3/2011 | Stevenson et al. | |
| 8,153,852 B2 * | 4/2012 | Ellis et al. ..................... | 585/418 |
| 2005/0197515 A1 | 9/2005 | Juttu et al. | |
| 2006/0011514 A1 | 1/2006 | van den Berge et al. | |
| 2006/0036120 A1 | 2/2006 | Corma Canos et al. | |
| 2008/0177119 A1 | 7/2008 | Juttu et al. | |
| 2008/0293987 A1 | 11/2008 | Khanmamedova et al. | |
| 2008/0293989 A1 | 11/2008 | Khanmamedova et al. | |
| 2008/0293990 A1 | 11/2008 | Stevenson et al. | |
| 2010/0280297 A1 | 11/2010 | Ellis et al. | |
| 2011/0132804 A1 | 6/2011 | Stevenson et al. | |
| 2011/0172479 A1 | 7/2011 | Stevenson et al. | |

FOREIGN PATENT DOCUMENTS

| | | |
|---|---|---|
| GB | 903773 | 8/1962 |
| GB | 1488936 | 10/1977 |
| JP | 62232487 | 10/1987 |
| WO | WO0018853 A1 | 4/2000 |

OTHER PUBLICATIONS

Flanigen, et al., Silicalite, A New Hydrophobic Crystalline Silica Molecular Sieve, Nature, vol. 271, Feb. 1978, pp. 512-516.
Cheng, et a., Synthesis, Characterization, and Growth Rates of Germanium Silicalite-1 Grown from Clear Solutions, J. Phys. Chem, B2006, 110, Oct. 3, 2006, pp. 21430-21437.
Written Opinion of the International Searching Authority in PCT/US2012/067525, Apr. 11, 2013, pp. 1-11.
International Search Report in PCT/US2012/067525, Apr. 11, 2013, pp. 1-5.

* cited by examiner

*Primary Examiner* — Elizabeth Wood
(74) *Attorney, Agent, or Firm* — Cantor Colburn LLP (57) ABSTRACT

A catalyst and its preparation and use are disclosed. The catalyst is a silicalite having germanium (Ge) included within the framework of the silicalite prepared in a particular manner. The catalyst may be used in a method of converting hydrocarbons wherein a hydrocarbon feed is contacted with the catalyst. The catalyst may be formed by preparing an aqueous reaction mixture of a silica-containing silicalite precursor material and a germanium source. The reactants of the reaction mixture are allowed to react. The reacted reaction mixture is heated under conditions to form crystals of a silicalite having germanium included within the framework of the silicalite. The crystals are then calcined to form the catalyst. In certain embodiments, a noble metal may be deposited upon the germanium-containing silicalite.

12 Claims, 2 Drawing Sheets

FIGURE 1. XRD pattern of calcined Ge-Silicalite

FIGURE 2

GERMANIUM SILICALITE CATALYST AND METHOD OF PREPARATION AND USE

FIELD OF THE INVENTION

The present invention relates to catalysts, their preparation and use, and particularly to those catalysts useful in the conversion of hydrocarbons.

BACKGROUND

A zeolite is a crystalline hydrated aluminosilicate that may also contain other metals in the crystalline framework of the zeolite crystal or deposited on its surface. The term "zeolite" includes not only aluminosilicates but substances in which the aluminum is replaced by other trivalent elements. Silicon may also be replaced by other tetravalent elements. Generally, zeolites are tetrahedra structures of the formula $TO_4$, which form a three dimensional network by sharing oxygen atoms and wherein T represents tetravalent elements, such as silicon, and trivalent elements, such as aluminum.

Zeolites are typically prepared by preparing an aqueous mixture of silicon oxide, aluminum oxide and, optionally, oxides of other trivalent or tetravalent elements; and maintaining the aqueous mixture under crystallization conditions until crystals of zeolite form. In the crystalline structure there are pores and channels which may be interconnected. The dimensions and configuration of these pores and channels allow access of molecules certain size or configuration, thus promoting the selectivity to certain products. Elements, such as metals, may be also deposited on the zeolite to facilitate selectivity or catalytic enhancement of the zeolite catalyst.

One particular use for zeolite catalysts is in the aromatization of alkanes and/or olefins. While useful zeolite catalysts for this process exist, improvements in zeolite catalysts that provide high selectivity for aromatics, or other products, and that provide high conversion with long catalyst life are still desired.

SUMMARY

A novel catalyst of a silicalite having germanium (Ge) included within the framework of the silicalite is provided that is prepared by preparing an aqueous reaction mixture of a silica-containing silicalite precursor material and a germanium source, allowing the reactants of the reaction mixture to react while maintaining a temperature of 55° C. or less, adjusting the pH of the reacted reaction mixture, if necessary, so that the reacted reaction mixture has a pH of 12 or less, and heating the reacted reaction mixture under conditions to form crystals of a silicalite having germanium included within the framework of the silicalite. The crystals are then calcined to form the final catalyst.

In certain embodiments, the germanium is present within the framework of the silicalite in an amount of from 8% or less by weight. In other embodiments, the germanium is present within the framework of the silicalite in an amount of from 3% or less by weight. The germanium may be present within the framework of the silicalite in an amount of at least 0.05% by weight.

In certain instances, any aluminum content of the silicalite may provide a silica/alumina molar ratio of 450:1 or greater. In still other embodiments, any aluminum content of the silicalite may provide a silica/alumina molar ratio of 600:1 or greater. And in still other embodiments, any aluminum content of the silicalite provides a silica/alumina molar ratio of 1000:1 or greater.

In certain embodiments, a noble metal may be deposited upon the germanium-containing silicalite. The noble metal may be present in an amount of from 0.05% to 3% by weight of the catalyst. In other instances, the noble metal may be present in an amount of from 0.1% to 2% by weight of catalyst. The noble metal may be platinum.

The catalyst may contain no fluorine or contain less than 0.01% by weight of any fluorine.

The pH of the reacted reaction mixture may also be adjusted to a pH of from 9 to less than 12 prior to heating the reacted reaction mixture. The reactants of the reaction mixture may be allowed to react while maintaining a temperature that does not exceed a temperature range of from 30° C. to 45° C.

A method of converting hydrocarbons is also provided. The method involves contacting a hydrocarbon feed with a catalyst comprising a silicalite having germanium (Ge) included within the framework of the silicalite, the catalyst having been prepared by preparing an aqueous reaction mixture of a silica-containing silicalite precursor material and a germanium source; allowing the reactants of the reaction mixture to react while maintaining a temperature of 55° C. or less; adjusting the pH of the reacted reaction mixture, if necessary, so that the reacted reaction mixture has a pH of 12 or less; and heating the reacted reaction mixture under conditions to form crystals of a silicalite having germanium included within the framework of the silicalite. The crystals are then calcined to form the final catalyst. A hydrocarbon feed is contacted with the catalyst under hydrocarbon conversion conditions to form hydrocarbon conversion products.

The germanium may be present within the framework of the silicalite in an amount of from 8% or less by weight. In other embodiments of the method, the germanium may be present within the framework of the silicalite in an amount of from 3% or less by weight. In still other embodiments, the germanium may be present within the framework of the silicalite in an amount of at least 0.05% by weight.

In certain instances of the method, any aluminum content of the silicalite may provide a silica/alumina molar ratio of 450:1 or greater. In still other embodiments, any aluminum content of the silicalite may provide a silica/alumina molar ratio of 600:1 or greater. And in still other embodiments, any aluminum content of the silicalite provides a silica/alumina molar ratio of 1000:1 or greater.

In certain embodiments of converting hydrocarbons, a noble metal may be deposited upon the germanium-containing silicalite. The noble metal may be present in an amount of from 0.05% to 3% by weight of the catalyst. In other instances, the noble metal may be present in an amount of from 0.1% to 2% by weight of catalyst. The noble metal may be platinum.

The catalyst may contain no fluorine or contain less than 0.01% by weight of any fluorine.

The pH of the reacted reaction mixture may also be adjusted to a pH of from 9 to less than 12 prior to heating the reacted reaction mixture. The reactants of the reaction mixture may be allowed to react while maintaining a temperature that does not exceed a temperature range of from 30° C. to 45° C.

In specific embodiments, the method of converting hydrocarbons may include using a hydrocarbon feed containing at least one of alkanes, olefins, and naphthenes having from 6 to 12 carbon atoms. The hydrocarbon conversion products may include aromatic compounds.

The invention also provides a method of forming a catalyst. The catalyst is formed by preparing an aqueous reaction mixture of a silica-containing silicalite precursor material and a germanium source, allowing the reactants of the reaction mixture to react while maintaining a temperature of 55° C. or less, adjusting the pH of the reacted reaction mixture, if necessary, so that the reacted reaction mixture has a pH of 12 or less, and heating the reacted reaction mixture under conditions to form crystals of a silicalite having germanium included within the framework of the silicalite. The crystals are then calcined to form the final catalyst.

The germanium source may be used in the reaction mixture in an amount that provides germanium within the framework of the silicalite crystals in an amount of from 8% or less by weight. In other instances, the germanium source is used in the reaction mixture in an amount that provides germanium within the framework of the silicalite crystals in an amount of from 3% or less by weight.

In certain embodiments, the reaction mixture further includes a structuring agent. The structuring agent may be an organic base, such as a tetralkylammonium hydroxide. The germanium source may be dispersed in a solution of the organic base prior to adding to the reaction mixture.

The reaction mixture may be substantially free from alkali- and alkali earth metals in certain embodiments.

The pH of the reacted reaction mixture may also be adjusted to a pH of from 9 to less than 12 prior to heating the reacted reaction mixture. The reactants of the reaction mixture may be allowed to react while maintaining a temperature that does not exceed a temperature range of from 30° C. to 45° C.

In more specific embodiments, the silica-containing silicalite precursor material may be dispersed in an aqueous fluid that is at a temperature of from 0° C. to 10° C., and wherein the germanium source and organic base are gradually added to the aqueous fluid of the silica-containing silicalite precursor material to form the aqueous reaction mixture. Water may also be added to the reaction mixture to complete reaction of the reaction mixture. Adjusting of the pH of the reacted reaction mixture to a pH of from 10 to 12 prior to heating the reacted reaction mixture may also take place. The reacted reaction mixture may be heated in an autoclave under pressure at a temperature of from 125° C. to 200° C. for a period of 10 days or less.

The method of forming the catalyst may also include depositing a noble metal upon the germanium-containing silicalite crystals. The noble metal may be deposited in an amount of from 0.05% to 3% by weight. In other instances, the noble metal may be deposited in an amount of from 0.1% to 2% by weight of catalyst. The noble metal may be platinum.

In the method of forming the catalyst, any aluminum content of the silicalite may provide a silica/alumina molar ratio of 450:1 or greater.

In certain embodiments, the reaction mixture may contain no fluorine ions.

The temperature of the reaction mixture may be maintained at a temperature of 55° C. or less by at least one of 1) cooling the reaction mixture, 2) controlling the rate of addition of the reactants, 3) controlling the amount of reactants added to the reaction mixture, 4) controlling the rate of mixing, and 5) controlling the temperature of at least one of the reactants added to the reaction mixture.

BRIEF DESCRIPTION OF THE DRAWINGS

For a more complete understanding of the present invention, and the advantages thereof, reference is now made to the following descriptions taken in conjunction with the accompanying figures, in which.

DETAILED DESCRIPTION

The ZSM-5 or MFI (mordenite framework inverted) zeolite is one of the most versatile zeolites used for catalysts in a variety of different reactions. The ZSM-5 zeolite is a porous material containing an intersecting two-dimensional pore structure with 10-membered oxygen rings. Zeolite materials with such 10-membered oxygen ring pore structures are often classified as medium-pore zeolites. The ZSM-5 zeolite catalysts and their preparation are described in U.S. Pat. No. 3,702,886, which is herein incorporated by reference. Such ZSM-5 zeolites are aluminosilicates that contain both silicon and aluminum in the crystalline structure.

ZSM-5 zeolites with germanium (Ge) incorporated into the framework have been developed. Such Ge/ZSM-5 zeolites may be useful in the preparation of aromatics from lower alkanes or olefins. For example, U.S. Pat. Nos. 6,784,333 and 7,902,413, which are each hereby incorporated herein by reference in its entirety for all purposes, each describe ZSM-5 zeolites with germanium incorporated into the framework of the zeolite. Such Ge/ZSM-5 zeolites are aluminosilicates containing both silicon and aluminum in the framework.

Silica compounds having crystalline structures that are the same or similar to ZSM-5 or MFI-type aluminosilicate zeolites have been developed. For instance, U.S. Pat. No. 4,061,724, incorporated herein by reference in its entirety for all purposes, describes such compounds. Such silica compounds are known in the art as "silicalites." Silicalites are also later described in the article presented in Nature, Vol. 271, *Silicalite, A New Hydrophobic Crystalline Silica Molecular Sieve*, E. M. Flanigen, et al., (February 1978), pp. 512-516, which is herein incorporated by reference for all purposes. As used herein, the term "silicalite" is meant to refer to those compositions described in U.S. Pat. No. 4,061,724. Such silicalites are formed from precursors of silica materials that contain little or no alumina ($Al_2O_3$). The inclusion of such alumina materials is considered to be an impurity in such silicalite precursors. Because commercially available silica sources typically are not completely free from such alumina compounds, there may be some amount of alumina in the silicalite as an impurity. For example, commercial silica sols may contain from about 500 to 700 ppm aluminum, while fumed silicas can contain from 80 to 2000 ppm of aluminum impurity. Such aluminum is typically present as $Al_2O_3$ in the silicalite product. While such small quantities of aluminum may exist, the silicalite containing such alumina or other oxide impurities can in no way be considered to be an aluminosilicate. If such alumina is present in the silica source, however, it may provide a silicalite crystalline structure that provides a silica/alumina molar ratio of about 450:1 or 500:1 or greater, more particularly from about 600:1, 700:1, 800:1, 900:1, 1000:1, 5000:1, 10,000:1 or higher.

It should be understood that with respect to any concentration or amount range listed or described in the summary or detailed description as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few data points, it is to be understood that the inventors appreciate and understand that any and all data points within the range are to be considered to have been specified, and that the inventors are in possession of the entire range and all points within the range.

While the formation of silicalite materials is known, the incorporation of germanium into the framework of such silicalite materials to provide an effective catalyst has not been achieved prior to the invention. In the present invention, germanium may be incorporated within the framework of the silicalite in an amount of from about 10%, 9%, 8% or less by weight. In particular embodiments, the germanium is incorporated in an amount of less than 3%, 2.5%, or 2% by weight. The lower limits of germanium incorporated into the framework of the silicalite is from 0.05%, 0.1%, 0.2%, 0.3%, 0.4%, or 0.5% by weight. Such silicalite incorporating germanium in the framework may be referred to herein as Ge/silicalite or similar designations and is contrasted with materials where germanium may be deposited on an already synthesized zeolite structure.

A noble metal may also be deposited on the Ge/silicalite. The noble metal may be deposited on the Ge/silicalite in an amount from about 0.05% to about 3% by weight of the Ge/silicalite catalyst. In particular embodiments, the noble metal may be deposited in an amount of from 0.1 or 0.2% to about 2% by weight. The noble metal may be any noble metal, non-limiting examples of which include platinum, palladium, iridium, rhodium, ruthenium, silver, and gold. In certain embodiments, the noble metal is platinum. The noble metal may also include combinations of different noble metals.

Other materials that may optionally be deposited on the Ge/silicalite may include rhenium (Re) and/or tin (Sn). These materials may be deposited in amounts of from about 0.01% to about 1% by weight of the Ge/silicalite catalyst.

The Ge/silicalite catalyst, with or without any deposited materials, may be bound with a suitable binding material. Such binding materials may include oxides of magnesium, aluminum, titanium, zirconium, thorium, silicon, boron, clay (e.g. kaolin, mont-morillonite, etc.), carbon (e.g. carbon black, graphite, activated carbon, carbon polymers, charcoal, etc.), a carbide (e.g. molybdenum carbide, silicon carbide, etc.), a metal nitride (e.g. tungsten nitride, etc.), zeolites, a metal oxide hydroxide (e.g. boehmite, etc.), and mixtures of these. The bound catalyst may contain from about 1 wt % to about 99 wt % of any binder material by total weight of the bound catalyst. In some applications the binder may be present in an amount of from about 10 wt % to about 50 wt % binder by total weight of bound catalyst.

To prepare the Ge/silicalite catalyst, an aqueous reaction mixture is prepared from a silica-containing silicalite precursor material and a germanium source. In certain embodiments, the reaction mixture may be substantially free from alkali- and alkali earth metals. In other embodiments, alkali- and alkali earth metals, such as sodium, may be present in the reaction mixture. The silicalite precursor is typically a source of silicon oxide. The precursor may be a tetraalkylorthosilicate, such as tetraethylorthosilicate (TEOS). The silica may also be silica in colloidal form, or a silicate of an alkaline metal, such as Na or K. Fumed silica or precipitated silica can also be used. The silica-containing silicalite precursor material is essentially free of aluminum, with any aluminum being present only as an impurity. It should be noted that in most cases, commercially available silicalite precursors will have some amount of aluminum present as an impurity. The silicalite precursor may have alumina present as an impurity in amounts of about 0.5%, 0.4%, 0.3%, 0.2%, 0.1% or less by weight of the silicalite precursor. An example of a suitable commercially available silicalite precursor is tetraethoxysilane, which is available from Alfa-Aesar, Ward Hill, Mass. and which is a tetraethyl ester of orthosilicic acid.

The germanium source may be any source of germanium compound that provides a tetravalent germanium oxide structure within the framework of the silicalite crystalline. A hydrolysable germanium compound may be used so that it is present in solution. Non-limiting examples of germanium sources include germanium oxide, germanium chloride, germanium isopropoxide, sodium germanate, and combinations of these. The germanium source is used in the reaction mixture in an amount that provides germanium within the framework of the silicalite crystals in those amounts described above.

The reaction mixture typically requires a structuring agent that facilitates placement of the germanium into the silicalite framework. The structuring agent controls the construction of the crystalline network and assists in stabilizing the structure. The structuring agent may be an organic compound, such as an organic base. Nitrogenated organic bases may be suitable for the structuring agent material. Examples of suitable structuring direction agent materials are the tetraalkylammonium hydroxides. In particular, tetrapropylammonium hydroxide (TPAOH) has been found to be a suitable structuring agent material. As is described in more detail later on, the organic structuring agent material may also serve as a solvent or dispersing fluid for the germanium source that is then added to the reaction mixture. Other structure directing agents may include ammonium ions, fluoride ions, and zeolite seed crystals. The structuring agent material may be used in an amount to provide a molar ratio of structuring agent/$SiO_2$ of from about 0.1 to about 1. In certain embodiments, no fluorine or less than 0.01% by weight fluorine is incorporated into the Ge/silicalite or otherwise used in the synthesis.

The reaction of the reagents to form the Ge/silicalite can be an exothermic hydrolysis reaction so that the temperature of the reaction mixture may rise rapidly if not controlled. This is particularly true when making larger quantities of the Ge/silicalite, on a laboratory scale, such as greater than 10 grams, 20 grams, 30 grams, or when making commercial quantities. The temperature of the reaction mixture may be controlled so that it does not exceed 55° C., 50° C., 45° C., 40° C., or 35° C. In many applications, the temperature will be controlled so that it does not exceed temperatures ranging from about 30° C. to about 45° C., more particularly from about 35° C. to about 40° C. To control the hydrolysis reaction the reactant mixture may be cooled during the reaction. In one particular method, the silicalite precursor material is initially cooled to a temperature of from about 0° C. to about 10° C., more particularly from about 0° C. to about 5° C. The germanium source along with the organic or other structuring agent material may then be admixed to this in a controlled or gradual manner so that the temperature of the reaction mixture does not rise too rapidly. In certain embodiments, the reaction temperature is controlled by rate and/or amount of reagent addition, the cooling rate, and/or the stirring or mixing rate, the cooling or controlling of the temperature of the reactants added to the reaction mixture, or a combination of these so that the reaction mixture temperature provides the desired properties in forming the silicalite materials. Additionally, cooling of the reactant mixture may be continued during the reaction, such as by placing the reactant mixture in a cooling bath or jacketed reaction vessel to control the reaction. If necessary, water may be added to the reaction mixture to complete the hydrolysis reaction in a molar ratio of water/$SiO_2$ of from about 10 to about 50, more particularly from about 20 to about 40.

The reagent components may be added and mixed in any sequence. For example, TEOS may be added to a solution of $GeO_2$ in TPAOH with or without inclusion of the rest of the water. Also, $GeO_2$ may be added to TEOS first, followed by the addition of TPAOH. In such cases, at least one of the components (e.g. TEOS or TPAOH) may be chilled or cooled.

The hydrolysis reaction is usually completed over a period of from about 2 hours to about 2 days.

After the hydrolysis reaction is complete, the pH of the reaction mixture may be at an elevated pH, such as a pH of about 12 or higher. The pH of the reacted reaction mixture may be controlled or adjusted to provide a pH of from about 9 to about 12 or less than 12, more particularly from about 10 or 10.5 to about 11.5 by the addition of a pH adjusting agent (e.g. acetic acid). Such pH range may be used without the inclusion of any fluorine ions. A higher pH may result in less germanium being incorporated into the silicalite structure.

The pH adjusted reacted mixture is then subjected to a hydrothermal treatment, wherein the reacted mixture is placed within an enclosed pressure vessel, such as an autoclave, where the reaction mixture is heated to a temperature of from about 100° C. to about 200° C. under its own pressure and stirred or mixed for a period of at least several hours, more particularly from about 1 day to about 10 days to form the Ge/silicalite crystals.

The resulting crystals are separated from any remaining reaction mixture liquids, such as through filtration and/or centrifugation. The crystals may be washed, such as with deionized water, dried, and calcined. Calcination may be conducted in an oxygen-containing atmosphere, such as air, at temperatures that may range from about 400° C. to about 600° C., which may be carried out for about 1 to about 20 hours.

In certain applications, a noble metal is deposited on the resulting Ge/silicalite catalyst. The noble metal and other deposited materials of Re and/or Sn, as described previously, may be deposited on the Ge/silicalite by any known methods. These may include ion exchange, impregnation and vapor deposition techniques. The Ge/silicalite with the deposited materials may also be calcined in an oxygen-containing atmosphere, such as air, at temperatures that may range from about 200° C. to about 450° C. and may be carried out for about 0.5 to about 10 hours.

The Ge/silicalite catalyst with or without any noble metal, such as platinum, or other deposited materials, may be bound with a binder, such as the binder materials described previously.

The above-described process steps of binding, depositing a noble metal or other materials, and calcining of the silicalite, with or without binder or with or without a noble metal can occur in any order.

The above-described Ge/silicalite catalysts are particularly useful in the conversion of hydrocarbon compounds. In such conversion, a hydrocarbon feed is contacted with the catalyst under hydrocarbon conversion conditions to form hydrocarbon conversion products. In one particular application, the hydrocarbon feed is composed of $C_6$ to $C_{12}$ hydrocarbons that undergo dehydrocyclization and/or dehydrogenation to form aromatic products. Such hydrocarbons may include light naphtha, which is typically considered the petroleum hydrocarbon fraction having a boiling point ranging from 30° C. to 160° C. The hydrocarbon compounds may include alkanes, olefins, naphthenes, and combinations of these. The Ge/silicalite catalyst incorporating a noble metal, such as platinum, has been found to be particularly useful in converting such hydrocarbon feed to aromatic compounds, such as benzene, toluene, and xylene.

In using the Ge/silicalite catalyst, a hydrocarbon feed to be treated may be introduced into a reactor containing the Ge/silicalite catalyst where the feed is contacted with the catalyst under hydrocarbon conversion conditions. Reaction conditions may vary, but in certain embodiments the temperature may range from about 400° C. to about 600° C., with pressures ranging from about 10 kPa to 10 MPa, and a LHSV ranging from about 0.5 to about 10 $hr^{-1}$.

The following examples better serve to illustrate the invention.

EXAMPLES

Example 1

Several Ge/silicalite zeolite catalyst materials were prepared with varying amounts of germanium. The different prepared materials were labeled as catalyst Samples A-I, the preparation of which is described below.

Sample A 0.19 g of $GeO_2$ (obtained from Umicore, catalyst grade) was dissolved in 39.6 g of tetrapropylammonium hydroxide (TPAOH) (40% solution in water; SACHEM). 36.93 g of TEOS (99.9%; Alfa-Aesar) was cooled down in an ice bath to 0° C. The $GeO_2$ solution was added dropwise into TEOS with vigorous stirring. The mixture was then taken out of the ice bath and deionized (D.I.) water (72 g) was added. In an unsealed container, the mixture was stirred at room temperature overnight. The resulting gel was acidified with 3.53 g of glacial acetic acid (99.7%; Aldrich) (pH=10.75).

Crystallization was made in a Teflon® lined autoclave at 175° C. with stirring (100 rpm) for 4 days (final pH=10.03).

The resulting material was filtered and washed on a filter with 4 L of D.I. water. After this, it was dried at 90° C. overnight and then was calcined in air at 550° C. for 10 hours. The analyzed content of germanium was 0.86 wt. %.

Platinum deposition over the Ge-silicalite at a target of 1 wt. % was made using incipient wetness impregnation from an aqueous solution of tetraammineplatinum (II) nitrate (Aldrich; >50.0% Pt basis). The impregnated sample was dried at 90° C. overnight and then calcined in air at 280° C. for 3 hours.

Sample B 0.89 g of $GeO_2$ was dissolved in 47.52 g of TPAOH. 44.27 g of TEOS was cooled down in an ice bath to 0° C. The $GeO_2$ solution was added dropwise into TEOS with vigorous stirring. The mixture was then taken out of the ice bath and D.I. water (86.4 g) was added. In an unsealed container, the mixture was stirred at room temperature overnight. The gel was acidified with 3.36 g of glacial acetic acid (pH=10.65).

Crystallization was made in a Teflon® lined autoclave at 175° C. with stirring (100 rpm) for 5 days (final pH=9.61).

The resulting material was filtered and washed on a filter with 3 L of D.I. water, and then dried at 90° C. overnight. This was then calcined in air at 550° C. for 6 hours. The analyzed content of germanium was 1.92 wt. %.

Platinum deposition was made as described for Sample A.

Sample C 0.72 g of $GeO_2$ was dissolved in 47.52 g of TPAOH. 44.26 g of TEOS was cooled down in an ice bath to 0° C. The $GeO_2$ solution was added dropwise into TEOS with vigorous stirring. The mixture was then taken out of the ice bath and D.I. water (86.4 g) was added. In an unsealed container, the mixture was stirred at room temperature overnight. The resulting gel was acidified with 4.04 g of glacial acetic acid (pH=11.04).

Crystallization was made in a Teflon® lined autoclave at 175° C. with stirring (100 rpm) for 5 days (final pH=9.51).

The resulting material was filtered and washed on a filter with 5 L of D.I. water, and then it was dried at 90° C. overnight and then was calcined in air at 550° C. for 10 hours. The analyzed content of germanium was 1.80 wt. %. An analysis of aluminum content was also made for this sample and showed an aluminum content of less than 15 ppm.

Platinum deposition was made as it was described for Sample A.

Sample D 1.10 g of $GeO_2$ was dissolved in 47.51 g of TPAOH. 44.27 g of TEOS was cooled down in an ice bath to 0° C. The $GeO_2$ solution was added dropwise into TEOS with vigorous stirring. The mixture was then taken out of the ice bath and D.I. water (86.4 g) was added. In an unsealed container, the mixture was stirred at room temperature overnight. The gel was acidified with 3.18 g of glacial acetic acid (pH=11.08).

Crystallization was made in a Teflon® lined autoclave at 175° C. with stirring (100 rpm) for 5 days (final pH=9.83).

The resulting material was filtered and washed on a filter with 4 L of D.I. water, and then dried at 90° C. overnight. This was then calcined in air at 550° C. for 10 hours. The analyzed content of germanium was 2.17 wt. %.

Platinum deposition was made as described for Sample A.

Sample E 1.48 g of $GeO_2$ was dissolved in 47.52 g of TPAOH. 44.27 g of TEOS was cooled down in an ice bath to 0° C. The $GeO_2$ solution was added dropwise into TEOS with vigorous stirring. The mixture was then taken out of the ice bath and D.I. water (86.4 g) was added. In an unsealed container, the mixture was stirred at room temperature overnight. The gel was acidified with 3.24 g of glacial acetic acid (pH=10.90).

Crystallization was made in a Teflon® lined autoclave at 175° C. with stirring (100 rpm) for 5 days (final pH=8.83).

The resulting material was filtered and washed on a filter with 3 L of D.I. water, and then dried at 90° C. overnight. This was then calcined in air at 550° C. for 10 hours. The analyzed content of germanium was 3.02 wt. %.

Platinum deposition was made as described for Sample A.

Sample F 4.45 g of $GeO_2$ was dissolved in 47.52 g of TPAOH. 44.27 g of TEOS was cooled down in an ice bath to 0° C. The $GeO_2$ solution was added dropwise into TEOS with vigorous stirring. The mixture was then taken out of the ice bath and D.I. water (86.4 g) was added. In an unsealed container, the mixture was stirred at room temperature overnight. The gel was acidified with 3.64 g of glacial acetic acid (pH=11.03).

Crystallization was made in a Teflon® lined autoclave at 175° C. with stirring (100 rpm) for 7 days (final pH=9.46).

The resulting material was filtered and washed on a filter with 4 L of D.I. water, and then dried at 90° C. overnight. This was then calcined in air at 550° C. for 10 hours. The analyzed content of germanium was 12.42 wt. %.

Platinum deposition was made as described for Sample A.

Comparative Sample G

As a comparison, a standard platinum-containing, Cs-exchanged GeZSM-5, which is known for use as an aromatization catalyst was used. The GeZSM-5 catalyst was prepared using standard preparation techniques. In the preparation, 10 grams of GeZSM-5 was washed with 400 ml of aqueous $CsNO_3$ (0.5M) then filtered. The filtrate was then rewashed 3 more times with 0.5M $CsNO_3$ then washed 3 times with 400 ml of distilled $H_2O$. The zeolite powder was then dried and calcined for 3 hours at 280° C. in air.

Platinum deposition was made using incipient wetness impregnation. This was carried out by adding dropwise a solution of 0.203 g $Pt(NH_2)_4(NO_3)_2$ dissolved in 5.20 g of deionized water to 10 grams of the Cs-exchanged GeZSM-5. The material was dried for 1 hour in a 110° C. drying oven then calcined in air at 280° C. for 3 hours. Elemental analysis gave 40.68 wt % Si, 0.78 wt % Al, 4.26 wt % Ge, 5.13, wt % Cs, and 0.93 wt % Pt.

Comparative Sample H

As a comparison, a silicalite was prepared without germanium. The silicalite without germanium was prepared by adding 47.52 g of TPAOH to 44.27 g of TEOS at room temperature, and then 86.4 g of D.I. water was added. The mixture was stirred for 24 hours. To this mixture 19.75 g of TPAOH was added.

The gel was acidified with 5.54 g of glacial acetic acid (pH=11.12).

Crystallization was made in Teflon® lined autoclave at 175° C. with stirring (100 rpm) for 4 days (final pH=8.09). The resulting material was filtered and washed on a filter with 4 L of D.I. water, and then dried at 90° C. overnight, followed by calcination in air at 550° C. for 10 hours. An analysis of aluminum content was also made for this sample and showed an aluminum content of less than 15 ppm.

Platinum deposition was made as it was described in Sample A.

Sample I 0.89 g of $GeO_2$ was dissolved in 47.52 g of TPAOH. The solution was cooled down in an ice bath to 0° C. 44.29 g of TEOS was cooled down in an ice bath to 0° C. TEOS was added dropwise into the $GeO_2$ solution with vigorous stirring. 0.75 g of NaCl was dissolved in 86.4 g of D.I. water. This solution was cooled down to 0° C., and then was introduced into the mixture with stirring for about 0.5 hour. In an unsealed container, the mixture was stirred at room temperature overnight. The white gel was acidified with 3.33 g of glacial acetic acid (pH=10.11).

Crystallization was made in a Teflon® lined autoclave at 175° C. with stirring (100 rpm) for 5 days (final pH=8.90).

The material was filtered and washed on filter with 4 L of D.I. water, and then dried at 90° C. overnight and calcined in air at 550° C. for 10 hours. The analyzed content of germanium was 2.28 wt. % and the content of sodium was 0.77 wt. %.

Platinum deposition was made as it was described in Sample A.

Figure 1:
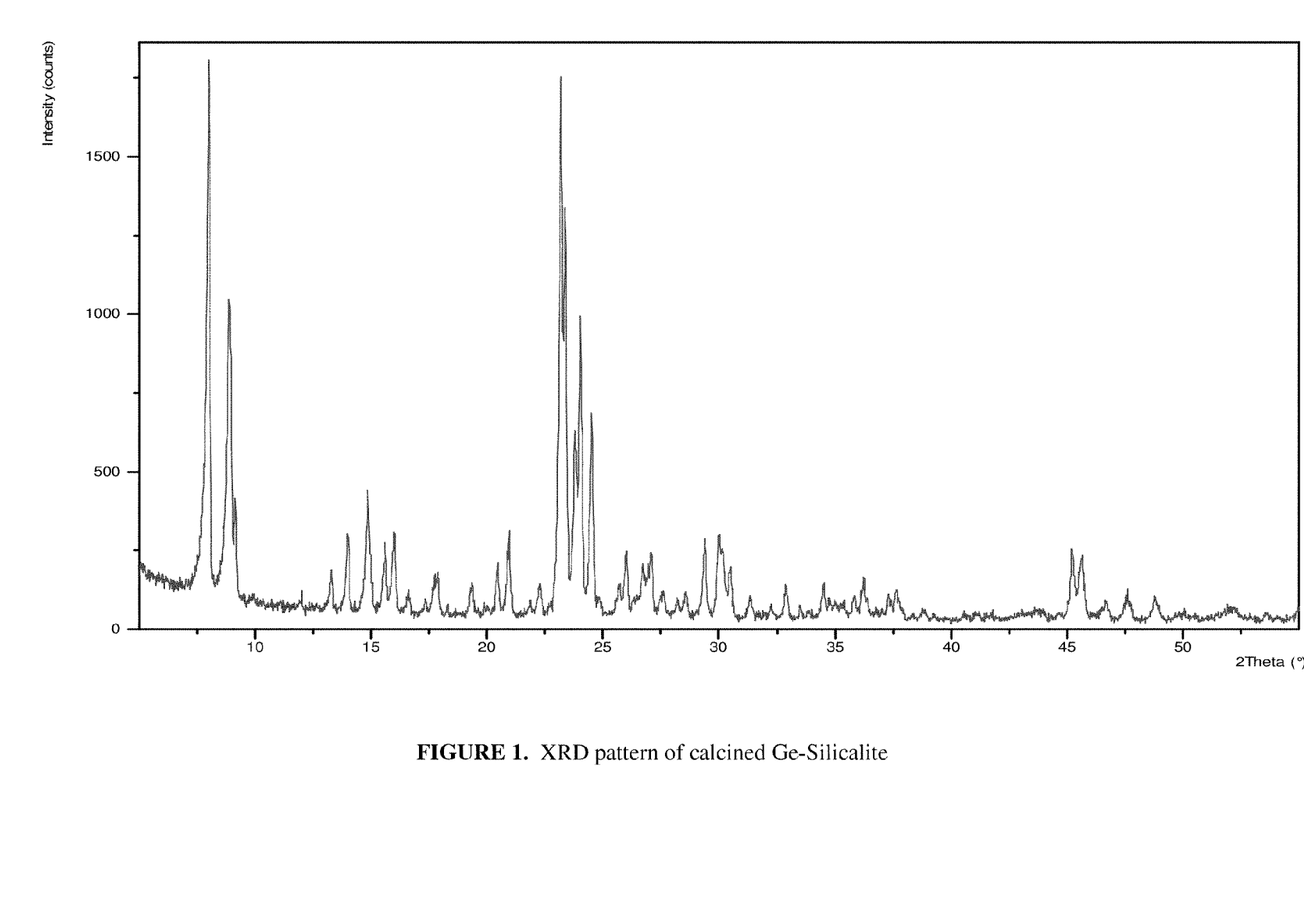
FIG. 1 is a XRD plot of a Ge/silicalite (Sample B) from Example 1, showing the crystalline structure of the Ge/silicalite being the same as that of a ZSM-5.

To determine the crystal structure of the prepared silicalite samples, Sample B was analyzed by XRD analysis and provided the plot shown in FIG. 1. This is consistent with the structure of a ZSM-5, thus confirming a ZSM-5 structure for the prepared Ge/silicalites.

The prepared samples were also analyzed by XRF analysis to determine their compositions prior to deposition with platinum. The results are presented in Table 1 below. As a comparative catalyst, the standard ZSM-5 zeolite (Sample G) catalyst that is commonly used in aromatization of light naphtha reactions was also analyzed by XRF analysis, with the results also being presented in Table 1. Comparative catalyst Sample H, which was the silicalite prepared without germanium, was not analyzed.

TABLE 1

| Sample | Si | Ge | Al | Si/Ge |
|---|---|---|---|---|
| | | Wt. % | | Mol. |
| Sample A | 45.68 | 0.86 | 0.00 | 138 |
| Sample B | 45.34 | 1.92 | 0.00 | 61 |
| Sample C | 45.04 | 1.80 | 0.00 | 65 |
| Sample D | 44.12 | 2.17 | 0.00 | 53 |
| Sample E | 44.08 | 3.02 | 0.00 | 38 |
| Sample F | 37.71 | 12.42 | 0.00 | 8 |
| Comparative Sample G | 42.37 | 5.62 | 0.74 | 20 |
| Comparative Sample H | — | — | — | — |
| Sample I | 43.84 | 2.28 | 0.00 | 50 |

Example 2

The prepared Ge/silicalites and comparative samples from Example 1 were analyzed by XRF analysis after treatment with platinum, with the results presented in Table 2 below to provide the final silicon and germanium content.

TABLE 2*

| Sample | Si | Ge |
|---|---|---|
| | Wt. % | |
| Sample A | 44.73 | 0.83 |
| Sample B | 44.71 | 1.88 |
| Sample C | 44.57 | 1.82 |
| Sample D | 44.61 | 2.17 |
| Sample E | 43.95 | 2.98 |
| Sample F | 36.66 | 13.63 |
| Comparative Sample G | 40.50 | 4.42 |
| Comparative Sample H | 46.29 | 0.00 |
| Sample I | 43.76 | 2.29 |

*Samples with Pt

Example 3

The platinum-containing catalyst samples prepared as described in Example 1 were each used in aromatization reactions using a fixed bed, continuous flow type reactor. For each sample, catalyst powder was pressed and sized to 20-40 mesh. A catalyst charge having a volume of 0.25 cm$^3$ at 0.127 g was mixed with 1.75 ml of inert silicon carbide chips and the mixture was loaded into a 0.194 (0.49 cm) inch ID plug flow reactor. The catalyst was pretreated at 460° C. for one hour in flowing H$_2$ gas. Catalyst testing was then started. A feed of n-hexane was vaporized into a stream of flowing hydrogen at a temperature of approximately 150° C. This gas mixture was passed through the reactor at a LHSV of 8.6 hr$^{-1}$, the reactor being maintained at a temperature of 515° C. by an external heating jacket.

The reaction products were analyzed by gas chromatography. Products ranging in size from methane to dimethylnaphthalene were observed. A variety of C$_6$ isomerization products were observed, including isohexanes (e.g. 2-methylpentane) and olefins (e.g. 1-hexene). For purposes of calculating conversion and selectivity, these C$_6$ products were considered to be unreacted. The selectivities reported are calculated as the sum of benzene, toluene, xylenes, and ethylbenzene products divided by the total amount of all benzene, C$_1$-C$_5$, and C$_7$+ materials recovered. These selectivities are presented on a molar C$_6$ basis in Table 3 below. The conversion and selectivities measured and presented in Table 3 are after approximately 50 hours on stream.

A quantitative measurement of the deactivation rate for each sample was also made. A first-order deactivation constant ($k_d$) was estimated by assuming that the rate of deactivation is proportional to conversion and is calculated using the conversion after 25 hours ($X_{25}$) and 50 hours ($X_{50}$) on stream and is represented by the equation for $k_d$ below:

$$k_d = 1000 \cdot \frac{\ln(X_{50}/X_{25})}{(50 - 25)}$$

The $k_d$ values for each catalyst are also presented in Table 3. Conversions and selectivities in Table 3 are those values measured after 50 hours on stream.

TABLE 3

| Sample | Si | Ge | Conversion | Selectivity | $k_d$ |
|---|---|---|---|---|---|
| | Wt. % | | Mol % | | |
| Sample A | 44.73 | 0.83 | 17 | 90 | −0.2 |
| Sample B | 44.71 | 1.88 | 21 | 92 | −1.1 |
| Sample C | 44.57 | 1.82 | 20 | 93 | −2.0 |
| Sample D | 44.61 | 2.17 | 18 | 91 | −2.1 |
| Sample E | 43.95 | 2.98 | 11 | 91 | −4.0 |
| Sample F | 36.66 | 13.63 | 1 | 45 | −10.5 |
| Comparative Sample G | 40.50 | 4.42 | 20 | 92 | −3.1 |
| Comparative Sample H | 46.29 | 0.00 | 7* | 81* | N/A |
| Sample I | 43.76 | 2.29 | 11 | 92 | −5.4 |

*Approximate data due to interrupted run.

As can be seen from Table 3, Samples A-E performed well, with good conversion and selectivity and were comparable to the standard Ge-ZSM-5 catalyst, i.e. Comparative Sample G. At higher levels of germanium content, i.e. Sample F, conversion and selectivity were much lower.

With respect to the $k_d$ values, the standard catalyst (Comparative Sample G), was tested 36 times. The average value of $k_d$ obtained was −3.06, with a standard deviation of 0.363. Applying a statistical t-test, the 95% confidence limits can be calculated to be −3.8 to −2.3 and the 99% confidence limits can be calculated to be −4.0 to −2.1.

For the first four samples (Samples A to D), all have $k_d$ values that are more (i.e., less negative) than the lower bound on the 95% confidence intervals, suggesting with a high degree of certainty that these catalysts deactivate at a significantly lower rate than the standard catalyst (Comparative Sample G). Based on this measurement, the deactivation rates of Sample C and Sample D are about one-third less than that of the standard catalyst Comparative Sample G. The deactivation rate of Sample B was roughly two-thirds less than that of the standard catalyst, and the deactivation rate of Sample A was near zero.

Example 4

To study the rate of deactivation of larger amounts of catalyst and at higher conversion, Sample B and the standard catalyst Comparative Sample G were each tested in aromatization reactions using a fixed bed, continuous flow type reactor. Similar procedures were used to those described for Example 3. For each sample, catalyst powder was pressed and sized to 20-40 mesh. A catalyst charge having a weight of 1.0 g and a volume of 2.16 cm³ (1.0 g) was mixed with 7.2 cm³ (11 g) of inert silicon carbide chips and was loaded into a 0.31 inch ID plug flow reactor. The catalyst was pretreated at 460° C. for one hour in flowing $H_2$ gas. Catalyst testing was then started. A feed of n-hexane was vaporized into a stream of flowing nitrogen at a temperature of approximately 150° C. This gas mixture was passed through the reactor at a LHSV of 2.0 hr$^{-1}$, the reactor being maintained at a temperature of 525° C. by an external heating jacket.

Figure 2:
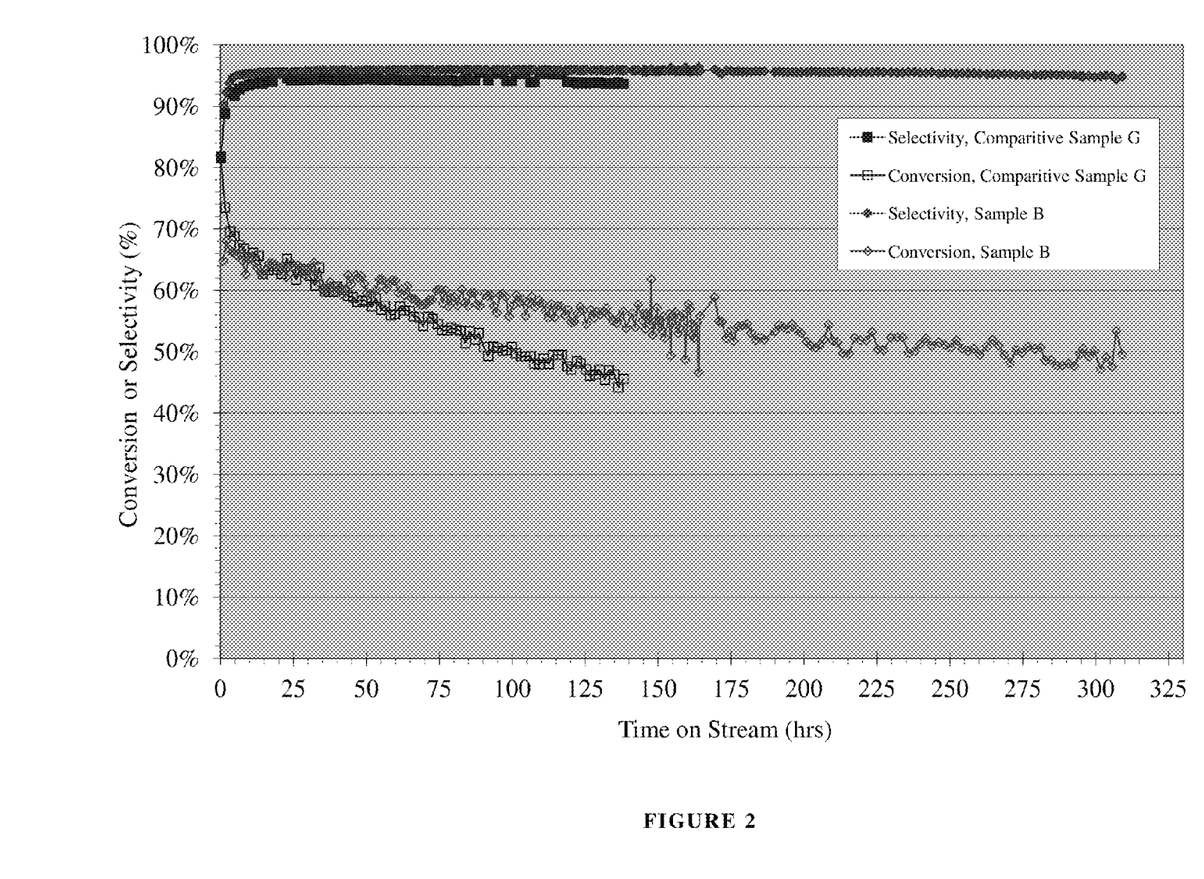
FIG. 2 is a plot of conversion and selectivity over time for Sample B and Comparative Sample G catalysts from Example 4 used in the conversion of n-hexane to $C_6$ aromatics.

A plot of catalyst activity and selectivity performance is presented in FIG. 2 for each sample. The important point from FIG. 2 is that conversion for Comparative Sample G continues to fall off well after the conversion for Sample B has largely stabilized and is falling off at a much slower rate.

Comparative Example 5

A Ge-silicalite with a Si/Ge molar ratio of 25 was prepared with 5.0 g of TEOS (Alfa-Aeser, 99.9%) mixed with 0.1005 g of $GeO_2$ (Aldrich, 99.999%) with stirring for 5 minutes. TPAOH (SACHEM, 40 wt. % in aqueous solution) was added to the mixture and vigorous stirring was continued for 30 minutes. Finally, 6.07 g of deionized water was then added and the whole mixture was aged for 24 hours at room temperature while mixing (pH=12.30). The solution was placed in a screw cap Teflon® container and heated at 368K for 7 days (pH=13.30). The solids were collected by centrifugation, washed with deionized water, dried at 90° C. overnight and calcined in air at 550° C. for 10 hours. Platinum was then deposited onto the prepared sample at a target 1 wt. % by incipient wetness impregnation using an aqueous solution of tetrammineplatinum (II) nitrate. XRF analysis data for the calcined Ge-silicalite (Sample J) and Pt/Ge-silicalite (Sample K) are presented in Table 4 below.

TABLE 4

| Sample | Si Wt. % | Ge Wt. % | Si/Ge Mol. |
|---|---|---|---|
| Comparative Sample J | 45.20 | 0.95 | 123 |
| Comparative Sample K | 44.56 | 0.94 | 123 |

Catalyst activity was tested for Sample K using the procedure described in Example 3. The results are presented in Table 5 below.

TABLE 5

| Catalyst | Conversion Mol % | Selectivity | $k_d$ |
|---|---|---|---|
| Comparative Sample K | 16 | 83 | −5.0 |

Comparative Example 6

A similar catalyst to that of Comparative Example 5 was prepared with the same materials but the amounts were scaled up approximately nine times. The catalyst was prepared by mixing 45.0 g. of TEOS with 0.9040 g $GeO_2$ with stirring for 5 minutes. TPAOH at 39.96 g was added to the mixture and vigorous stirring was continued for 30 minutes. The temperature of the mixture was monitored during stirring and recorded with the rise in temperature presented in Table 6 below. The maximum temperature of 65° C. was observed at approximately 11 minutes after TPAOH addition. It is noted that no observable temperature increase was measured in Comparative Example 5 and is likely due to the rather small amount of reactants used.

TABLE 6

| Time (minutes) | Temperature (° C.) |
|---|---|
| Start | 24 |
| 5 | 26 |
| 10 | 39 |
| 11 | 65 |
| 20 | 46 |
| 33 | 33 |

After 30 minutes of stirring, the temperature of the mixture was 33° C. Deionized water at 54.63 g was then added and the whole mixture was aged for 24 hours at room temperature while mixing (pH=12.04). The solution was placed in a 300 ml Parr autoclave with a Teflon® liner and heated at 368K for 13 days (pH=12.88). The solids were collected by centrifugation, washed with deionized water, and dried at 90° C. overnight and calcined in air 550° C. for 10 hours. Platinum was then deposited onto the prepared sample at a target 1 wt. % by incipient wetness impregnation using an aqueous solution of tetrammineplatinum (II) nitrate. XRF analysis data for the calcined Ge-silicalite (Comparative Sample L) and Pt/Ge-silicalite (Comparative Sample M) are presented in Table 7 below.

TABLE 7

| Sample | Si Wt. % | Ge Wt. % | Si/Ge Mol. |
|---|---|---|---|
| Comparative Sample L | 45.26 | 1.73 | 68 |
| Comparative Sample M | 44.98 | 1.70 | 69 |

Catalyst activity was tested for Comparative Sample M using the procedure described in Example 3. The results are presented in Table 8 below. As can be seen, there was no conversion when using Comparative Sample M.

TABLE 8

| Catalyst | Conversion Mol % | Selectivity | $k_d$ |
|---|---|---|---|
| Comparative Sample M | 0 | — | — |

Comparative Example 7

28 g of a 40% aqueous solution of TPAOH was diluted with 45 g of water and to this solution was added 4 g of $GeO_2$ (Umicore, 99.99% $GeO_2$) and 6.12 g of silica (Aerosil 150 marketed by Degussa). The mixture was permitted to equilibrate at 60° C. for 2 hours. The mixture was heated at 160° C. for 3 days in an autoclave. After cooling, filtration, washing and drying at 90° C. overnight, the sample was calcined in air at 550° C. for 10 hours. Platinum was then deposited onto the prepared sample at a target 1 wt. % by incipient wetness impregnation using an aqueous solution of tetrammineplatinum (II) nitrate. XRF analysis data for the calcined Ge-silicalite (Comparative Sample N) and Pt/Ge-silicalite (Comparative Sample O) are presented in Table 9 below.

TABLE 9

| Sample | Si Wt. % | Ge Wt. % | Si/Ge Mol. |
|---|---|---|---|
| Comparative Sample N | 41.55 | 8.74 | 12 |
| Comparative Sample O | 40.34 | 8.53 | 12 |

Catalyst activity was tested for Comparative Sample O using the procedure described in Example 3. The results are presented in Table 10 below.

TABLE 10

| Catalyst | Conversion Mol % | Selectivity | $k_d$ |
|---|---|---|---|
| Comparative Sample O | 0 | — | — |

Comparative Example 8

A similar catalyst to that of Comparative Example 7 was prepared using the same materials but with a lower amount of germanium, i.e. Si/Ge=25 versus Si/Ge=2.66. 28 g of a 40% aqueous solution of TPAOH was diluted with 45 g of water and to this solution was added 0.4262 g of $GeO_2$ (Umicore, 99.99% $GeO_2$) and 6.12 g of silica (Aerosil 150 marketed by Degussa). The mixture was permitted to equilibrate at 60° C. for 2 hours. The mixture was heated at 160° C. for 3 days in an autoclave. After cooling, filtration, washing and drying at 90° C. overnight, the sample was calcined in air at 550° C. for 10 hours. Platinum was then deposited onto the prepared sample at a target 1 wt. % by incipient wetness impregnation using an aqueous solution of tetrammineplatinum (II) nitrate. XRF analysis data for the calcined Ge-silicalite (Comparative Sample P) and Pt/Ge-silicalite (Comparative Sample Q) are presented in Table 11 below.

TABLE 11

| Sample | Si Wt. % | Ge Wt. % | Si/Ge Mol. |
|---|---|---|---|
| Comparative Sample P | 44.91 | 1.68 | 69 |
| Comparative Sample Q | 44.29 | 1.65 | 70 |

Catalyst activity was tested for Sample Q using the procedure described in Example 3. The results are presented in Table 12 below.

TABLE 12

| Catalyst | Conversion Mol % | Selectivity | $k_d$ |
|---|---|---|---|
| Comparative Sample Q | 9 | 90 | −4.0 |

Example 9

Comparative Samples R and S were prepared in a manner similar to that of examples C and B except that the mixture was not cooled and the temperature was allowed to increase from room temperature.

For Comparative Sample R, a solution of 0.72 g of $GeO_2$ in 47.52 g of TPAOH at room temperature was added dropwise to 44.26 g of TEOS at room temperature over 60 minutes with vigorous stirring. A temperature increase of the mixture up to 80° C. was recorded with formation of condensed particles. After that 86.4 g of D.I. water was added. The mixture was stirred at room temperature for 18 hrs. The mixture was acidified with glacial acetic acid (3.33 g) to adjust to a pH=11.13. Crystallization was made at 175° C. with stirring at 100 rpm for 3 days. The standard procedure of sample washing, drying/calcinations, and Pt deposition as for Sample A was applied.

For Comparative Sample S, 44.28 g of TEOS at room temperature was added dropwise to a solution of 0.89 g of $GeO_2$ in 47.52 g of TPAOH at room temperature over 45 minutes with vigorous stirring. A temperature increase of the mixture up to 57° C. was recorded. After that 86.4 g of D.I. water was added. The mixture was stirred at room temperature for 16 hrs. The mixture was acidified with glacial acetic acid (2.87 g) to adjust to a pH=10.49. Crystallization was made at 175° C. with stirring at 100 rpm for 4 days. The standard procedure of sample washing, drying/calcinations, and Pt deposition as for Sample A was applied.

For Sample T, 44.26 g of TEOS at room temperature was added dropwise to a solution of 0.72 g of $GeO_2$ in 47.52 g of TPAOH at room temperature over 60 minutes with vigorous stirring. A temperature increase of the mixture up to 45° C. was recorded. After that 86.4 g of D.I. water was added. The mixture was stirred at room temperature for 18 hrs. The mixture was acidified with glacial acetic acid (3.33 g) to adjust pH to 11.01. Crystallization was made at 175° C. with stirring at 100 rpm for 3 days. The standard procedure of sample washing, drying/calcinations, and Pt deposition as for Sample A was applied.

Samples R-T were each used in aromatization reactions using a fixed bed, continuous flow type reactor using the procedures described for Example 3. The results, along with the germanium content of the catalysts, are presented in Table 13 below. As can be seen, for comparative Samples R and S the conversion was lower compared to those samples prepared with cooling. For Sample T, which was not initially cooled but the temperature was only allowed to rise to 45° C. the performance was improved over the comparative examples, but not as good as in those examples where the reaction mixture was initially cooled below room temperature.

TABLE 13

| Sample | Ge content in catalyst Wt. % | Conversion Mol % | Selectivity | $k_d$ |
|---|---|---|---|---|
| Comparative Sample R | 1.50 | 7 | 78 | −5.2 |
| Comparative Sample S | 2.78 | 6 | 86 | −9.6 |
| Sample T | 1.39 | 9 | 90 | −3.6 |

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:
1. A catalyst comprising:
   a silicalite having germanium (Ge) in a amount if from about 8% or less by weight included within the framework of the silicalite prepared by:
   preparing an aqueous reaction mixture of a silica-containing silicalite precursor material and a germanium source;

allowing the reactants of the reaction mixture to react while maintaining a temperature of 55° C. or less;

adjusting the pH of the reacted reaction mixture, if necessary, so that the reacted reaction mixture has a pH of 12 or less;

heating the reacted reaction mixture under conditions to form crystals of a silicalite having germanium included within the framework of the silicalite; and calcining the crystals.

2. The catalyst of claim 1, wherein:
the germanium is present within the framework of the silicalite in an amount of from about 3% or less by weight.

3. The catalyst of claim 1, wherein:
the germanium is present within the framework of the silicalite in an amount of at least about 0.05% by weight.

4. The catalyst of claim 1, wherein:
any aluminum content of the silicalite provides a silica/alumina molar ratio of about 450:1 or greater.

5. The catalyst of claim 1, wherein:
any aluminum content of the silicalite provides a silica/alumina molar ratio of about 1000:1 or greater.

6. The catalyst of claim 1, further comprising:
a noble metal deposited upon the germanium-containing silicalite.

7. The catalyst of claim 6, wherein:
the noble metal is present in an amount of from about 0.05% to about 3% by weight of the catalyst.

8. The catalyst of claim 6, wherein:
the noble metal is present in an amount of from about 0.1% to about 2% by weight of catalyst.

9. The catalyst of claim 6, wherein:
the noble metal is platinum.

10. The catalyst of claim 1, wherein:
the catalyst contains no or less than 0.01% by weight of any fluorine.

11. The catalyst of claim 1, wherein:
the pH of the reacted reaction mixture is adjusted to a pH of from about 9 to less than 12 prior to heating the reacted reaction mixture.

12. The catalyst of claim 1, wherein:
the reactants of the reaction mixture are allowed to react while maintaining a temperature that does not exceed a temperature range of from about 30° C. to about 45° C.

\* \* \* \* \*